(12) United States Patent
Goshen

(10) Patent No.: US 10,463,331 B2
(45) Date of Patent: Nov. 5, 2019

(54) APPARATUS FOR MULTI MATERIAL DECOMPOSITION

(71) Applicant: KONINKLIJKE PHILIPS N.V., Eindhoven (NL)

(72) Inventor: Liran Goshen, Pardes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/762,109

(22) PCT Filed: Aug. 28, 2017

(86) PCT No.: PCT/EP2017/071508
§ 371 (c)(1),
(2) Date: Mar. 22, 2018

(87) PCT Pub. No.: WO2018/046328
PCT Pub. Date: Mar. 15, 2018

(65) Prior Publication Data
US 2019/0069865 A1   Mar. 7, 2019

(30) Foreign Application Priority Data

Sep. 8, 2016   (EP) ..................... 16187835

(51) Int. Cl.
*A61B 6/00* (2006.01)
*A61B 6/03* (2006.01)
*A61B 6/02* (2006.01)

(52) U.S. Cl.
CPC .............. *A61B 6/482* (2013.01); *A61B 6/032* (2013.01); *A61B 6/5205* (2013.01); *A61B 6/025* (2013.01); *A61B 6/405* (2013.01); *A61B 6/4241* (2013.01)

(58) Field of Classification Search
CPC ......... A61B 6/025; A61B 6/032; A61B 6/405; A61B 6/4241; A61B 6/482; A61B 6/483;
(Continued)

(56) References Cited

U.S. PATENT DOCUMENTS 8,306,180 B2   11/2012   Zhang
8,311,181 B2   11/2012   Thomsen
(Continued)

OTHER PUBLICATIONS

Li, et al., "Image-based material decomposition with a general volume constraint for photon-counting CT", Progress in Biomedical Optics and Imaging, SPIE International Society for Optical Engineering, vol. 9412, Mar. 18, 2015.
(Continued)

*Primary Examiner* — Chih-Cheng Kao
(74) *Attorney, Agent, or Firm* — Larry Liberchuk

(57) ABSTRACT

The present invention relates to an apparatus for multi material decomposition of an object. It is described to provide (310) at least one image of an object. The at least one image is derived from at least one spectral X-ray image of the object, and the at least one image comprises a Photoelectric total attenuation coefficient image and a Compton scattering total attenuation coefficient image. A plurality of Photoelectric attenuation coefficients are provided (320) for a plurality of materials, each Photoelectric attenuation coefficient being associated with a corresponding material. A plurality of Compton scattering attenuation coefficients are provided (330) for the plurality of materials, each Compton scattering attenuation coefficient being associated with a corresponding material. A total volume constraint is set (340) at an image location in the at least one image as a function of the sum of individual volumes of the plurality of materials at the image location. Volume fractions of the plurality of materials are determined (350) at the image location according to an overall function comprising:
(Continued)

a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint. Data representative of the volume fractions of the plurality of materials is output (360).

13 Claims, 3 Drawing Sheets

(58) Field of Classification Search
CPC .. A61B 6/5205; A61B 6/5282; G01N 23/046; G01N 23/20066
See application file for complete search history.

(56) References Cited

U.S. PATENT DOCUMENTS

| | | | |
|---|---|---|---|
| 9,036,879 | B2 | 5/2015 | Mendonca |
| 2008/0135789 | A1 | 6/2008 | Du |
| 2008/0253504 | A1 | 10/2008 | Proksa |
| 2008/0310598 | A1 | 12/2008 | Zhang |
| 2012/0134531 | A1* | 5/2012 | Zhang .................. A61B 6/032 382/100 |
| 2015/0071400 | A1 | 3/2015 | Popescu |
| 2015/0363947 | A1 | 12/2015 | Rigie |
| 2018/0120241 | A1* | 5/2018 | Seetho ................ G01N 23/046 |

OTHER PUBLICATIONS

Xu, et al., "Sparsity-regularized image reconstruction of decomposed K-edge data in spectral CT", Physics in Medicine and Biology, vol. 59, No. 10, Apr. 28, 2014.
Mendonça, et al., "Multi-material decomposition of spectral CT images." SPIE Medical Imaging. International Society for Optics and Photonics, 2010.
Long, et al. "Multi-material decomposition using statistical image reconstruction in X-ray CT." Proc. 2nd Int. Mtg. on image formation in X-ray CT (2012): 413-6.
Mendonça, Paulo RS, Peter Lamb, and Dushyant V. Sahani. "A flexible method for multi-material decomposition of dual-energy CT images." Medical Imaging, IEEE Transactions on 33.1 (2014): 99-116.
Alvarez, et al,. "Energy selective reconstructions in X-ray Computerized Tomography", Physics in medicine and biology, 21(5), 733-744, 1976.
Johnson, et,al,. "Medical Radiology/Diagnostic Imaging: Dual Energy Ct in Clinical Practice", Springer, 2011.
Nakada, et al., "Joint estimation of tissue types and linear attenuation coefficients for photon counting CT", Med. Phys. 42 (9), Sep. 2015.
Yu, et al., "A Novel Weighted Total Difference Based Image Reconstruction Algorithm for Few-View Computed Tomography", (2014).
Mechlem et al., "Dictionary-based image denoising for dual energy computed tomography"; (2016).
Lu, et al., "Few-view image reconstruction with dual dictionaries"; (2012).
Zhao, et al. "Dual-Dictionary Learning-Based Iterative Image Reconstruction for Spectral Computed Tomography Application"; (2015).
Zhang, et al., "Few-View Image Reconstruction Combining Total Variation and a High-Order Norm"; (2013).

\* cited by examiner

APPARATUS FOR MULTI MATERIAL DECOMPOSITION

CROSS REFERENCE TO RELATED APPLICATIONS

This application is the U.S. National Phase application under 35 U.S.C. § 371 of International Application No. PCT/EP2017/071508, filed Aug. 28, 2017, published as WO 2018/046328 on Mar. 16, 2018, which claims the benefit of European Patent Application Number 16187835.0 filed Sep. 8, 2016. These applications are hereby incorporated by reference herein.

FIELD OF THE INVENTION

The present invention relates to an apparatus for multi material decomposition of an object, to a system for multi material decomposition of an object, to a method for multi material decomposition of an object, as well as to a computer program element and a computer readable medium.

BACKGROUND OF THE INVENTION

The general background of this invention is the field of X-ray spectral computed tomography (CT). In a CT system an X-ray source emits X-ray radiation. The emitted radiation traverses an examination region with a subject or object located within and is detected by a detector array opposite the X-ray source. The detector array detects the radiation traversing the examination region and the subject and generates projection data, e.g. raw detector data or projection images. A reconstructor processes the projection data and reconstructs a volumetric image of the subject or object. X-ray Spectral CT is an imaging modality that extends the capabilities of a conventional CT system. Dual-Energy (DE) CT, which is a specific configuration of spectral CT, utilizes two attenuation values acquired at two photon energies to solve the photoelectric and Compton contribution that consists of the mass attenuation coefficient of a material, and thus to identify an unknown material by its value of photoelectric and Compton contribution. This scheme works especially well in materials such as iodine that has k-edge energy close to the mean value of a diagnostic energy range. Because any two linearly independent sums of two basis functions span the entire attenuation coefficient space, any material can be represented by a linear combination of two other materials, so called basis materials, such as water and iodine. The basis material images provide new applications such as monochromatic image, material cancellation image, effective atomic number image and electron density image. There are several approaches to perform dual energy CT acquisition such as dual-source, fast kVp switching, and dual-layer detector configurations. In addition, quantitative imaging is one of the current major trends in the medical imaging community. Spectral CT supports this trend, as the additional spectral information improves the quantitative information that can be measured about the scanned object and its material composition.

Such Multi Material Decomposition (MMD) is becoming a fundamental task for many clinical applications, in which the goal is often to characterize, detect and/or quantify the amount of a given material. MMD for DE CT is very challenging, because as discussed above, as there are only two acquired energy attenuations in principle two materials can be decomposed accurately. By further constraining the problem, three materials can be decomposed. However, utilizing DE CT for decomposition for more than three materials is an ill-posed problem.

US2008/0253504A1 relates to a CT system for determining the quantitative material concentrations of the components, such as bone, blood, contrast agent, in a region of interest of an object, such as a patient. To provide a CT system which improves the quality and explanatory power of quantitative material decomposition, a CT system is proposed comprising: a scanning unit having a radiation source and a detector unit for acquisition of spectral CT projection data from said region of interest; a modeling unit for obtaining a photoelectric effect projection data set and a Compton effect projection data set by decommodeling unit posing said spectral CT projection data set by means of respective models of photoelectric effect and Compton effect; a reconstruction unit for reconstructing a photoelectric effect image and a Compton effect image of said region of interest from said photoelectric effect projection data set and Compton effect projection data set; a processing unit for determining the concentrations of said components in said region of interest by solving a system of equations obtained by equating said photoelectric effect image data with the accumulated products of said concentrations and photoelectric attenuation coefficients for said components and equating said Compton effect image data with the accumulated products of said concentrations and Compton attenuation coefficients for said components.

Further information relating to MMD can be found in the following documents: Mendonça, Paulo R S, et al. "Multi-material decomposition of spectral CT images." SPIE Medical Imaging. International Society for Optics and Photonics, 2010; Long, Yong, and Jeffrey A. Fessler. "Multi-material decomposition using statistical image reconstruction in X-ray CT." Proc. 2nd Int. Mtg. on image formation in X-ray CT (2012): 413-6; and Mendonça, Paulo R S, Peter Lamb, and Dushyant V. Sahani. "A flexible method for multi-material decomposition of dual-energy CT images." Medical Imaging, IEEE Transactions on 33.1 (2014): 99-116.

SUMMARY OF THE INVENTION

It would be advantageous to have improved apparatus for multi material decomposition of an object.

The object of the present invention is solved with the subject matter of the independent claims, wherein further embodiments are incorporated in the dependent claims. It should be noted that the following described aspects and examples of the invention apply also for multi material decomposition of an object, the system for multi material decomposition of an object, the method for multi material decomposition of an object and for the computer program element and the computer readable medium.

According to a first aspect, there is provided an apparatus for multi material decomposition of an object, comprising:
an input unit;
a processing unit; and
an output unit.

The input unit is configured to provide the processing unit with at least one image of an object. The at least one image is derived from at least one dual energy spectral X-ray image of the object. The at least one image comprises a Photoelectric total attenuation coefficient image and a Compton scattering total attenuation coefficient image. The input unit is configured to provide the processing unit with a plurality of Photoelectric attenuation coefficients for a plurality of materials that comprises at least four materials, each Photoelectric attenuation coefficient being associated with a corresponding material. The input unit is also configured to provide the processing unit with a plurality of Compton scattering attenuation coefficients for the plurality of materials, each Compton scattering attenuation coefficient being associated with a corresponding material. The processing unit is configured to set a total volume constraint at an image location in the at least one image as a function of the sum of individual volumes of the plurality of materials at the image location. The processing unit is also configured to determine volume fractions of the plurality of materials at the image location according to an overall function comprising: a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint. An iterative minimization algorithm is used to solve the overall function. The output unit is configured to output data representative of the volume fractions of the plurality of materials.

In this manner, dual energy computer tomography imagery can be used to provide for material decomposition into four or more materials. In other words, the object can be represented by four or more different material types, and dual energy computer tomography imagery can be used to provide 4 or more images of the object, each characterized by a different material type.

In other words, dual energy computer tomography imagery can be used in combination with a dictionary of materials, and a volume conservation constraint, with total variation regularization and sparse decomposition mechanisms being able to be utilized to solve an optimization problem in order to provide for material decomposition into four or more materials.

To put this another way, dual energy imagery can be used to perform fast, automatic, accurate and robust multi material decomposition.

In an example, the overall function comprises a Total Variation term determined according to a function comprising the plurality of Photoelectric attenuation coefficients for the plurality of materials and the plurality of Compton scattering attenuation coefficients for the plurality of materials.

In an example, the Total Variation term comprises a Photoelectric coefficient for a material of the plurality of materials being added to a Compton scattering coefficient for that material.

In an example, the Total Variation term comprises a summation over the plurality of materials, wherein the summation comprises each Photoelectric coefficient for the plurality of materials being added to a corresponding Compton scattering coefficient for the plurality of materials.

In an example, the overall function comprises a Sparsity term determined according to a function comprising: the Photoelectric total attenuation coefficient at the image location; the Compton scattering total attenuation coefficient at the image location; the plurality of Photoelectric attenuation coefficients for the plurality of materials; and the plurality of Compton scattering attenuation coefficients for the plurality of materials.

In an example, the Sparsity term comprises the Photoelectric total attenuation coefficient at the image location being subtracted from a Photoelectric attenuation coefficient for a material of the plurality of materials, and the Sparsity term comprises the Compton scattering total attenuation coefficient at the image location being subtracted from a Compton scattering attenuation coefficient for the material of the plurality of materials.

In an example, the Sparsity term comprises information about the expected volume fraction of at least one of the materials.

In an example, the overall function comprises a data fidelity term determined according to a function comprising: the Photoelectric total attenuation coefficient at the image location; the Compton scattering total attenuation coefficient at the image location; the plurality of Photoelectric attenuation coefficients for the plurality of materials; and the plurality of Compton scattering attenuation coefficients for the plurality of materials.

In an example, the data fidelity term comprises a summation over all of the materials of a Photoelectric attenuation coefficient for a material of the plurality of materials multiplied by a volume fraction of that material. This summation is subtracted from the Photoelectric total attenuation coefficient at the image location. Also, the data fidelity term comprises a summation over all of the materials of a Compton scattering attenuation coefficient for a material of the plurality of materials multiplied by a volume fraction of that material. This summation is subtracted from the Compton scattering total attenuation coefficient at the image location.

In an example, the processing unit is configured to generate the at least one image of the object from a decomposition of the at least one spectral X-ray image of the object.

In other words, dual energy X-ray imagery is decomposed into one image comprising Photoelectric attenuation coefficients at each pixel position, for a determined energy, and into a second image comprising Compton scattering attenuation coefficients at each pixel position, for the determined energy. To put this another way, the dual energy data are used to determine basis functions in the form of weighted versions of photoelectric and Compton scattering total cross-sections at image pixel positions.

According to a second aspect, there is provided a medical system for multi material decomposition of an object, the system comprising:
 an image acquisition unit; and
 an apparatus for multi material decomposition of an object according to the first aspect.

The image acquisition unit is configured to acquire the at least one dual energy spectral X-ray image of the object. The processing unit is configured to determine volume fractions of the plurality of materials at a plurality of image locations. The output unit is configured to output at least one image of the object on the basis of the plurality of volume fractions of the plurality of materials.

According to a third aspect, there is provided a method for multi material decomposition of an object, comprising:
a) providing at least one image of an object, wherein the at least one image is derived from at least one dual energy spectral X-ray image of the object, and wherein the at least one image comprises a Photoelectric total attenuation coefficient image and a Compton scattering total attenuation coefficient image;
b) providing a plurality of Photoelectric attenuation coefficients for a plurality of materials, each Photoelectric attenuation coefficient being associated with a corresponding material;

c) providing a plurality of Compton scattering attenuation coefficients for the plurality of materials, each Compton scattering attenuation coefficient being associated with a corresponding material;
d) setting a total volume constraint at an image location in the at least one image as a function of the sum of individual volumes of the plurality of materials at the image location;
e) determining volume fractions of the plurality of materials at the image location according to an overall function comprising: a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint, wherein, an iterative minimization algorithm is used to solve the overall function; and
f) outputting data representative of the volume fractions of the plurality of materials, wherein the plurality of materials comprises at least four materials.

In this manner the algorithm can be applied to imagery of objects such as body parts as well as to phantoms.

According to another aspect, there is provided a computer program element controlling apparatus as previously described which, in the computer program element is executed by processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
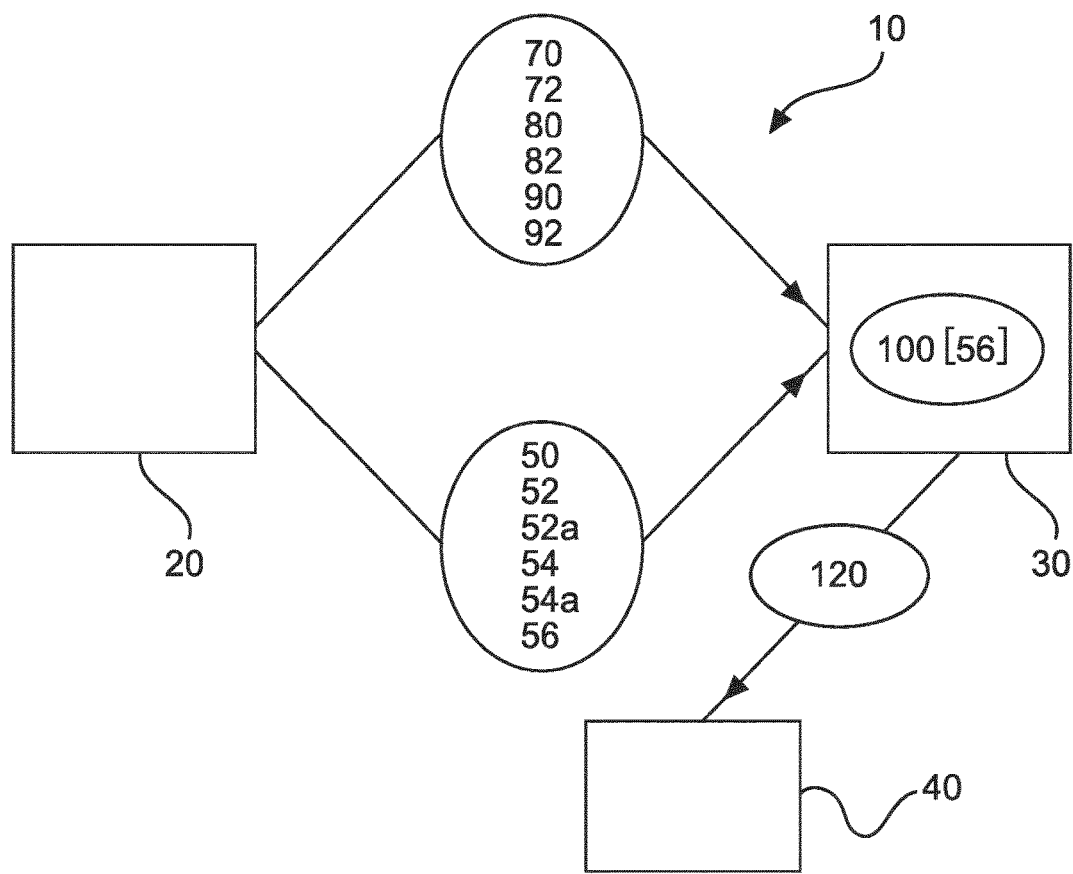
FIG. 1 shows a schematic set up of an example of an apparatus for multi material decomposition of an object.

FIG. 1 shows an example of an apparatus 10 for multi material decomposition of an object. The apparatus 10 comprises an input unit 20, a processing unit 30, and an output unit 40. The input unit 20 is configured to provide the processing unit 30 with at least one image 50 of an object. The at least one image 50 is derived from at least one spectral X-ray image 60 of the object. The at least one image 50 comprises a Photoelectric total attenuation coefficient image 52 and a Compton scattering total attenuation coefficient image 54. The input unit 20 is also configured to provide the processing unit 30 with a plurality of Photoelectric attenuation coefficients 70 for a plurality of materials 80, each Photoelectric attenuation coefficient being associated with a corresponding material. The input unit 20 is also configured to provide the processing unit 30 with a plurality of Compton scattering attenuation coefficients 90 for the plurality of materials 80, each Compton scattering attenuation coefficient being associated with a corresponding material. The processing unit 30 is configured to set a total volume constraint 100 at an image location 56 in the at least one image 50 as a function of the sum of individual volumes of the plurality of materials at the image location. The processing unit 30 is also configured to determine volume fractions 120 of the plurality of materials at the image location according to an overall function comprising: a Photoelectric total attenuation coefficient 52a at the image location 56 taken from the Photoelectric total attenuation coefficient image 52; a Compton scattering total attenuation coefficient 54a at the image location 56 taken from the Compton scattering total attenuation coefficient image 54; the plurality of Photoelectric attenuation coefficients 70 for the plurality of materials 80; the plurality of Compton scattering attenuation coefficients 90 for the plurality of materials 80; and the total volume constraint 100. The output unit 40 is configured to output data representative of the volume fractions 120 of the plurality of materials 80.

In an example, the Photoelectric total attenuation coefficient image is an image comprising effective Photoelectric attenuation coefficients at each pixel position (voxel) for an effective material at that pixel position that would have this attenuation coefficient—in other words the actual constituent materials at a pixel position has resulted in an effective attenuation coefficient as if those mix of materials was one material. The same is true for the Compton scattering image.

In an example, the apparatus can be used in tomosynthesis imaging or image display. In this manner, in an example the apparatus can be applied to X-ray Tomosynthesis.

In an example, the apparatus can be used in tomosynthesis imaging or image display. In an example, the apparatus can be used in digital tomosynthesis imaging or image display.

In an example, the apparatus can be applied to conventional, attenuation, X-ray imaging and in this way can provide for imaging of more than three materials in an object, as well as mitigate beam hardening effects in the acquired images.

In an example, the at least one image is derived from at least one spectral X-ray image that was acquired through the use of an energy-resolving photon counting detector. In other words, an X-ray source operating at more than one energy at one time can be used to simultaneously provide for acquisition of dual energy imagery. In an example, a dual source configuration, and/or a fast kVp switching scan configuration is used in acquiring the dual energy imagery, where imagery at two energies need not be acquired simultaneously.

In other words, as the at least one image is derived from at least one spectral X-ray image, the apparatus can be used in a post-processing mode relating to previously acquired spectral imagery.

In an example, the total volume constraint comprises the term $(1-\Sigma_{i=1}^{n}M_i)^2$, i.e., the assumption is made that the sum of the volumes of the constituent materials is equivalent to the volume of the mixture.

In an example, the plurality of materials comprises at least 4 materials.

In an example, the object is a body part, such as a body part of a human subject. In an example, the object is an inanimate object being examined or that has been examined, such as in machine part inspection during non-destructive testing or a piece of luggage being inspected at an airport or port.

According to an example, the overall function comprises a Total Variation term determined according to a function comprising the plurality of Photoelectric attenuation coefficients 70 for the plurality of materials 80 and the plurality of Compton scattering attenuation coefficients 90 for the plurality of materials 80.

According to an example, the Total Variation term comprises a Photoelectric coefficient 72 for a material 82 of the plurality of materials 80 being added to a Compton scattering coefficient 92 for that material 82.

In an example, a Photoelectric coefficient for material i (also termed 82) of a plurality of materials n (also termed 80) is written as $p_i$ (also termed 72) and a Compton scattering coefficient for material i is written as $s_i$ (also termed 92) and the Total Variation term comprises a weight factor $w_i^g = p_i + s_i$. In an example, the Total Variation term comprises a roughness penalty of a volume fraction to be minimized expressed as $w_i^g |\nabla M_i|$, wherein Mi is the volume fraction of material i.

According to an example, the Total Variation term comprises a summation over the plurality of materials. The summation comprises each Photoelectric coefficient 70 for the plurality of materials 80 being added to a corresponding Compton scattering coefficient 90 for the plurality of materials.

In an example, the Total variation term comprises the summation.

$$\Sigma_{i=1}^{n} w_i^g |\nabla M_i|.$$

According to an example, the overall function comprises a Sparsity term determined according to a function comprising: the Photoelectric total attenuation coefficient 52a at the image location 56; the Compton scattering total attenuation coefficient 54a at the image location 56; the plurality of Photoelectric attenuation coefficients 70 for the plurality of materials 80; and the plurality of Compton scattering attenuation coefficients 90 for the plurality of materials 80.

According to an example, the Sparsity term comprises the Photoelectric total attenuation coefficient 52a at the image location 56 being subtracted from a Photoelectric attenuation coefficient 72 for a material 82 of the plurality of materials 80. The Sparsity term also comprises the Compton scattering total attenuation coefficient 54a at the image location 56 being subtracted from a Compton scattering attenuation coefficient 92 for the material 82 of the plurality of materials 80.

In an example, a Photoelectric coefficient for material i (of a plurality of materials n) is written as $p_i$ and a Compton scattering coefficient for material i is written as $s_i$ and the Photoelectric total attenuation coefficient at the image location is written as P (also termed 52a) and the Compton scattering total attenuation coefficient at the image location is written as S (also termed 54a) and the Sparsity term comprises a weight factor $$w_i = \sqrt{(p_i - P)^2 + (s_i - S)^2}.$$

In an example, the Sparsity term comprises the term $\Sigma_{i=1}^{n} w_i M_i$, where Mi is the volume fraction of material i. In this manner, a solution can be provided with sparse combinations of materials from a predetermined material dictionary (or library, or data store).

According to an example, the Sparsity term comprises information about the expected volume fraction of at least one of the materials.

In an example, the material weight, $w_i$, can be used to introduce prior information to the algorithm, e.g., if there is a prior knowledge about the expected volume of material i in the scanned object, the material weight, $w_i$, could be adjusted accordingly.

According to an example, the overall function comprises a data fidelity term determined according to a function comprising: the Photoelectric total attenuation coefficient 52a at the image location 56; the Compton scattering total attenuation coefficient 54a at the image location 56; the plurality of Photoelectric attenuation coefficients 70 for the plurality of materials 80; and the plurality of Compton scattering attenuation coefficients 90 for the plurality of materials 80.

According to an example, the data fidelity term comprises a summation over all of the materials 80 of a Photoelectric attenuation coefficient 70 for a material of the plurality of materials 80 multiplied by a volume fraction of that material. This summation is subtracted from the Photoelectric total attenuation coefficient 52a at the image location 56. The data fidelity term also comprises a summation over all of the materials 80 of a Compton scattering attenuation coefficient 90 for a material of the plurality of materials 80 multiplied by a volume fraction of that material. This summation is subtracted from the Compton scattering total attenuation coefficient 54a at the image location.

In an example, there are a pair of spectral basis images that where derived using spectral basis decomposition. The two images are a Photoelectric image and a Compton scattering image, wherein the total Photoelectric coefficient at the image location (pixel position) is termed P and the total Compton scattering coefficient at the image location is termed S. In addition, a dictionary of n materials is given, where for material i in the dictionary, $p_i$ and $s_i$ are the attenuation coefficient of the material in the Photoelectric and Compton scattering images, correspondingly. In this example, the overall function is solved using the following joint optimization problem:

$$(\widetilde{M_1}, ..., \widetilde{M_n}) = \operatorname*{argmin}_{(M_1,...,M_n)} \int \Sigma_{i=1}^{n} w_i^g |\nabla M_i| + \frac{1}{2}\beta \int ((P - \Sigma_{i=1}^{n} p_i M_i)^2 + (S - \Sigma_{i=1}^{n} s_i M_i)^2) + \frac{1}{2}\lambda \int (1 - \Sigma_{i=1}^{n} M_i)^2 + \alpha \int \Sigma_{i=1}^{n} w_i \circ M_i$$

subject to $$M_i \geq 0 \;\; \forall \, i \in \{1, ..., n\}$$

$$M_i \leq t_i \;\; \forall \, i \in \{1, ..., n\}$$

where $M_i$ is the volume fraction map of material i, i.e., the volume fraction of material i in the mix of materials of the scanned object; $w_i^g$ is a TV weight factor (e.g., $w_i^g = p_i + s_i$), $w_i$ is a sparsity and prior information weight factor (e.g., $w_i = \sqrt{(p_i - P)^2 + (s_i - S)^2}$); $\beta$, $\lambda$ and $\alpha$ are control parameters that may be adjusted to provide different tradeoffs between the functional terms; $\circ$ is the Hadamard product and $t_i$ is an upper threshold for material i.

According to an example, an iterative minimization algorithm is used to solve the overall function.

In an example, an iterative alternating minimization algorithm is utilized in which the value of the functional always decreases. The algorithm is stated as follows:

Iterate the following alternating material maps updates:
for m=1 to n $$M_m(i) = \frac{w_m^g \Sigma_D \frac{M_m(D)}{\psi(D)} + \beta p_m(p - \Sigma_{q \neq m} p_q M_q(i)) + \beta s_m(s - \Sigma_{q \neq m} S_q M_q(i)) + \lambda(1 - \Sigma_{q \neq m} M_q(i)) - \alpha w_m(i)}{w_m^g \Sigma_{D} 1/\psi(D) + \beta(p_m^2 + s_m^2) + \lambda}$$

where D is the set of directions {E, N, W, S, U, D}, i is the index of the current voxel (image location) in the volume (at least one image), and the weight of direction 'E' is given as follows:

$$\psi(E) = \sqrt{\frac{(M_m(E) - M_m(i))^2}{d_y^2} + \frac{(M_m(NE) - M_m(SE) + M_m(N) - M_m(S))^2}{(4d_x)^2} + \frac{(M_m(U) + M_m(EU) - M_m(D) - M_m(ED))^2}{(4d_z)^2} + \varepsilon}$$

where $\varepsilon$ is a small number, e.g., $\varepsilon = 0.001$, and $d_x$, $d_y$ & $d_z$ are the voxel (image location) dimensions.

The weights for the other directions are derived in analogous manner.
if $M_m(i) < 0$ than set $M_m(i) = 0$
end According to an example, the processing unit is configured to generate the at least one image of the object from a decomposition of the at least one spectral X-ray image of the object.

Figure 2:
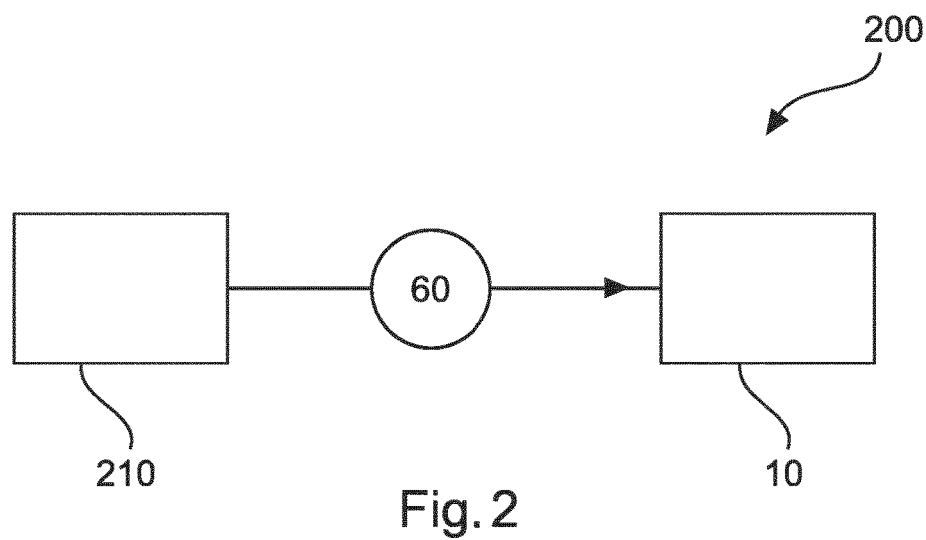
FIG. 2 shows a schematic set up of an example of a system for multi material decomposition of an object.

FIG. 2 shows a medical system 200 for multi material decomposition of an object. The system 200 comprises an image acquisition unit 210, and an apparatus 10 for multi material decomposition of an object as described with reference to FIG. 1. The image acquisition unit 210 is configured to acquire the at least one spectral X-ray image 60 of the object. The processing unit 20 is configured to determine volume fractions of the plurality of materials at a plurality of image locations. The output unit 40 is configured to output at least one image of the object on the basis of the plurality of volume fractions of the plurality of materials.

In an example, the image acquisition unit comprises an X-ray imaging device, for example, a tomosynthesis arrangement.

Figure 3:
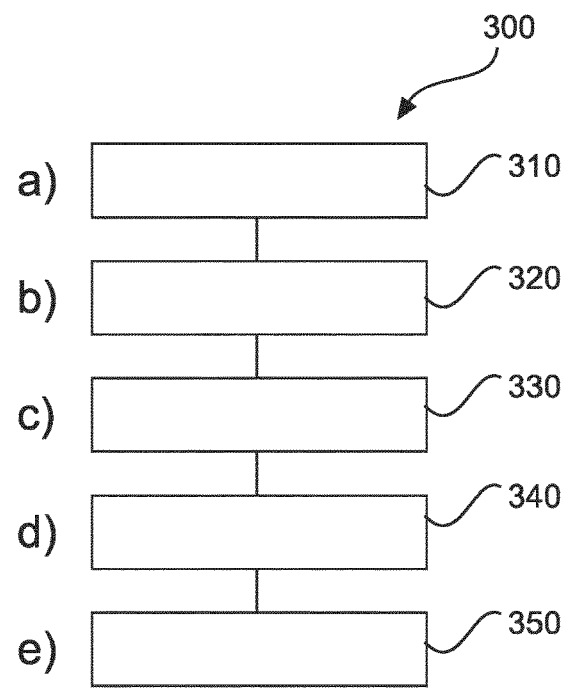
FIG. 3 shows a method for multi material decomposition of an object.

FIG. 3 shows a method 300 for multi material decomposition of an object in its basic steps. The method 300 comprising:

in a providing step 310, also referred to as step a), at least one image of an object is provided, wherein the at least one image is derived from at least one spectral X-ray image of the object, and wherein the at least one image comprises a Photoelectric total attenuation coefficient image and a Compton scattering total attenuation coefficient image; in a providing step 320, also referred to as step b), a plurality of Photoelectric attenuation coefficients for a plurality of materials are provided, each Photoelectric attenuation coefficient being associated with a corresponding material;

in a providing step 330, also referred to as step c), a plurality of Compton scattering attenuation coefficients for the plurality of materials are provided, each Compton scattering attenuation coefficient being associated with a corresponding material;

in a setting step 340, also referred to as step d), a total volume constraint at an image location in the at least one image is set as a function of the sum of individual volumes of the plurality of materials at the image location;

in a determining step 350, also referred to as step e), volume fractions of the plurality of materials at the image location are determined according to an overall function comprising: a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint; and in an outputting step 360, also referred to as step f), data representative of the volume fractions of the plurality of materials is output.

Examples of the apparatus, system and method for multi material decomposition of an object will now be described in more detail in conjunction with FIGS. 4-5.

Figure 4:
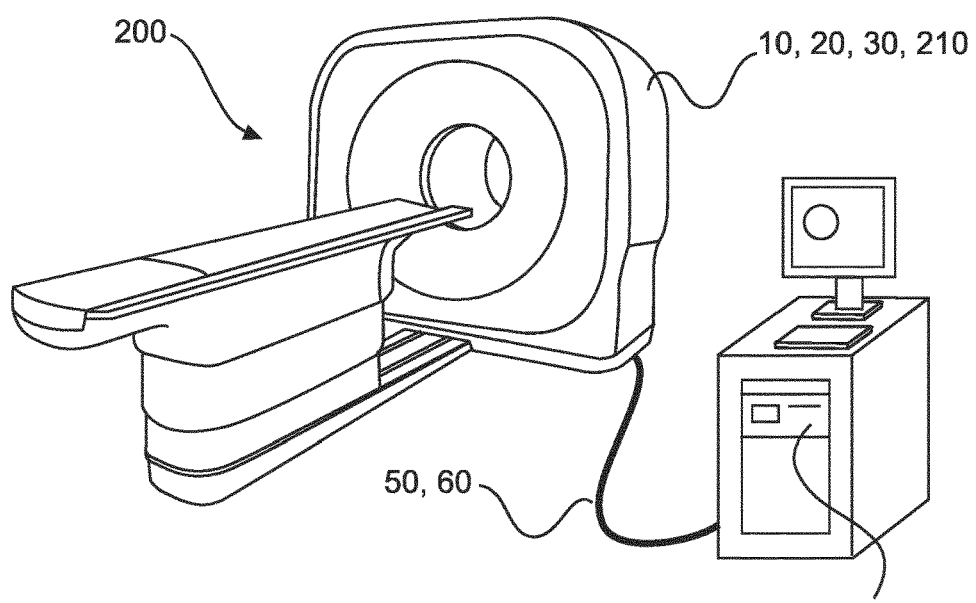
FIG. 4 shows a schematic set up of an example of a system for multi material decomposition of an object.

FIG. 4 shows an example of a system 200 for multi material decomposition of an object. In this example, the object is a body part of a human or animal and could be the whole body. The skilled person would however appreciate that the object could be a piece of luggage being examined at an airport or port, or be a component being examined during non-destructive testing for example. The system 200 includes an image acquisition unit 210, such as an X-ray computed tomography scanner. The system 200 is configured to generate spectral projection data and decompose that spectral data into basis sets. The image acquisition unit 210 includes one or more X-ray sources, such as an X-ray tube which emits radiation that traverses an examination region shown in the center of the acquisition unit 210. The X-ray source(s) can be two X-ray sources operating at, and potentially switching between, different voltages or an X-ray source that is switching between two voltages (e.g. 80 and 100 kV, or 100 and 120 kV). The X-ray source can be a source that emits broadband X-ray radiation over a range of energies. A detector opposite the X-ray sources detects the radiation that traverses the examination region. The detector can generate projection data for each voltage, when the source or sources are operating at different voltages at different times, or an energy resolving detector can be used to simultaneously acquire spectral projection data at different energies for two X-ray sources operating at the same time, or for a broadband X-ray source. Such an energy resolving dual layer detector is shown in FIG. 5. A patient can lie on a table which moves into the examination region, and spectral projection data of one or more body parts and indeed of the whole body if necessary can be generated/acquired. The projection data can be represented as at least one projection image (at least one spectral X-ray image) 60. A decomposition unit, housed within the image acquisition unit or within a separate workstation, decomposes the at least one spectral X-ray image 60, or spectral data, into at least one basis image 50 such as: photoelectric attenuation image 52 and Compton attenuation coefficient image 54; water and Iodine components; water and Calcium components; or acetal homopolymer resin, e.g. Delrin® and tin components; and/or other basis images. Thus the at least one spectral image 60 can be passed via a communication cable from the image acquisition unit to the workstation and this is used to derive the at least one image 50, or the at least one image 50 is generated from the at least one spectral image 60 within the image acquisition unit 210 and passed via the communication cable to the workstation. The workstation has access to a library (dictionary) of Compton scattering and photoelectric coefficients for various materials, and at the energies of operation of the image acquisition unit. Additionally, information relating to the expected contribution of a particular material, or a number of different materials, within a body part can be input into the workstation, where this prior knowledge can be used when performing material decomposition. For example, an operator may know for a fact that half of the volume of a part of an object, or indeed of the whole object, is made up of a particular material. An apparatus 10 for multi material decomposition, as described with reference to FIG. 1, is partially housed within the image acquisition unit 210 and the workstation, means that all of the parts of the apparatus 10 can be housed within the image acquisition unit or the some parts of the apparatus can be in the image acquisition unit and some in the work station, or completely housed within the workstation. The apparatus 10 takes the basis images 52 and 54, and uses the library of scattering attenuation coefficient values along with any prior information and volume constraint information, and these images are processed at each voxel to decompose the body into multiple materials at those voxels (volume pixels) within the body part imagery. Decomposed imagery, such as four or more separate images of different material types of one or more images with more than one material shown within that image can be presented on the workstation and/or transmitted externally.

Figure 5:
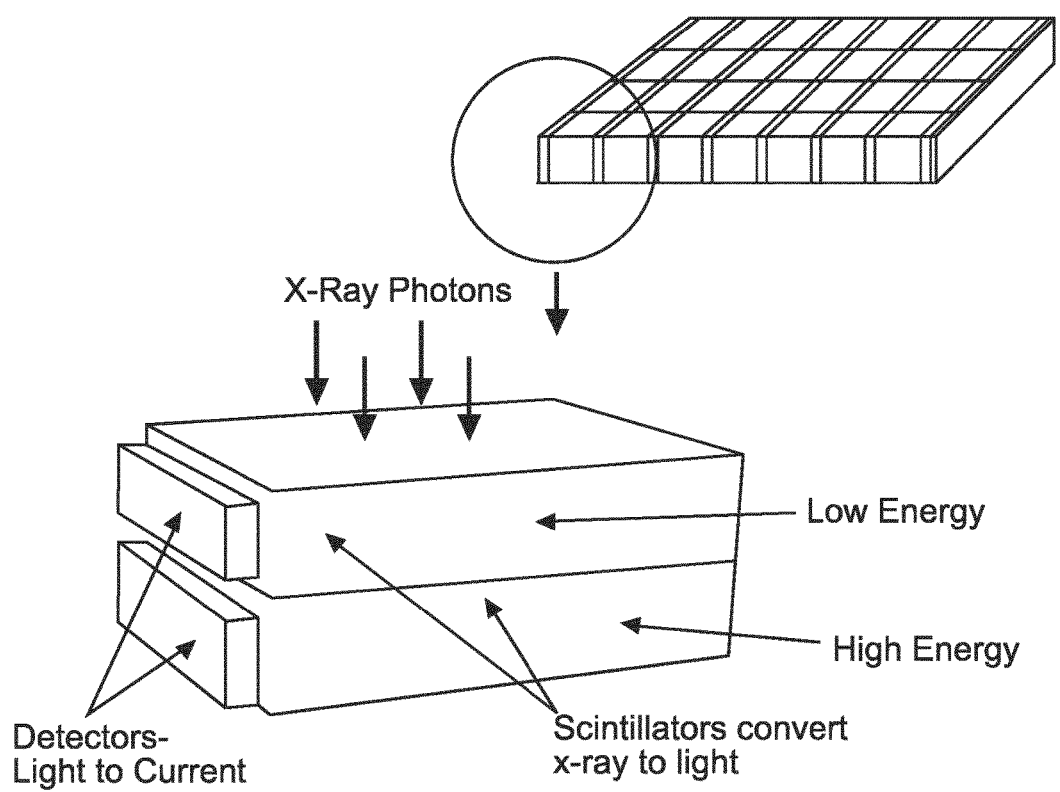
FIG. 5 shows an example of a dual energy detector.

FIG. 5 shows a dual layer detector array, which is a stack of two scintillators that are used to obtain spectral information by different effective spectral sensitivities of the layers, with one pixel of that array shown in an expanded view. A detector pixel is made from two scintillators stacked one on top of the other, with X-rays being incident from the top. Low energy X-rays are absorbed in the top scintillators, with absorption leading to the emission of longer wavelength radiation that is detected by a photodiode that is positioned on the lateral side of that scintillator. The bottom scintillator absorbs high energy X-rays and again re-emitted longer wavelength radiation is detected by a second photodiode associated with that scintillator.

The following is a detailed description of the algorithm and model used for multi material decomposition as used within the apparatus, system and method for multi material decomposition of an object. As discussed above, the object could be a body part, or a part of a body part of a human or animal, but could also be an inanimate object and the algorithm can be used on phantoms.

Algorithm Inputs

As discussed above, the input to the segmentation algorithm can be acquired using any of the current common DE scan approaches, e.g., dual-source configuration, fast kVp switching scan or dual-layer detector configuration.

MMD Model

To recall, a pair of spectral basis images P and S are provided, that were derived using spectral basis decomposition e.g., Photoelectric and Compton scattering images. More information on spectral basis decomposition can be found in the following document: Alvarez, R., & Macovski, A. (1976). Energy selective reconstructions in X-ray Computerized Tomography, Physics in medicine and biology, 21(5), 733-744. In addition, a dictionary of n materials is given, where for material i in the dictionary, $p_i$ and $s_i$ are the attenuation coefficient of the material in the Photoelectric and Compton scattering images, correspondingly. For this situation, MMD is modeled using the following joint optimization problem:

$$(\widetilde{M_1}, \ldots, \widetilde{M_n}) = \operatorname*{argmin}_{(M_1, \ldots, M_n)} \int \Sigma_{i=1}^n w_i^g |\nabla M_i| + \frac{1}{2}\beta \int ((P - \Sigma_{i=1}^n p_i M_i)^2 + (S - \Sigma_{i=1}^n s_i M_i)^2) + \frac{1}{2}\lambda \int (1 - \Sigma_{i=1}^n M_i)^2 + \alpha \int \Sigma_{i=1}^n w_i \circ M_i$$

subject to $$M_i \geq 0 \ \forall i \in \{1, \ldots, n\}$$

$$M_i \leq t_i \ \forall i \in \{1, \ldots, n\}$$

where $M_i$ is the volume fraction map of material i, i.e., the volume fraction of material i in the mix of materials of the scanned object; $w_i^g$ is a TV weight factor (e.g., $w_i^g = p_i + s_i$), $w_i$ is a sparsity and prior information weight factor (e.g., $w_i = \sqrt{(p_i - P)^2 + (s_i - S)^2}$); $\beta$, $\lambda$ and $\alpha$ are control parameters that are adjusted to provide different tradeoffs between the functional terms; $\circ$ is the Hadamard product and $t_i$ is an upper threshold for material i.

In this optimization problem, the weighted TV term $w_i^g |\nabla M_i|$ express the roughness penalty of the material volume fraction map to be minimized. The term $((P - \Sigma_{i=1}^n p_i M_i)^2 + (S - \Sigma_{i=1}^n s_i M_i)^2)$ is the data fidelity term. The term $(1 - \Sigma_{i=1}^n M_i)^2$ is the volume conservation constraint, i.e., assuming the sum of the volumes of the constituent materials is equivalent to the volume of the mixture. The $L_1$ norm term $\Sigma_{i=1}^n w_i M_i$ leads to a solution with sparse combinations of materials from the predetermined material dictionary (or library). In addition, the material weight, $w_i$, can be used to introduce prior information to the algorithm, e.g., if there is a prior knowledge about the expected volume of material i in the scanned object, the material weight, $w_i$, can be adjusted accordingly.

Alternating Minimization Algorithm

For the above optimization problem in the above equation, an iterative alternating minimization algorithm is developed in which the value of the functional always decreases.

The algorithm is stated as follows:

Iterate the following alternating material maps updates:

for m=1 to n $$M_m(i) = \frac{w_m^g \Sigma_D \frac{M_m(D)}{\psi(D)} + \beta p_m(p - \Sigma_{q \neq m} p_q M_q(i)) + \beta s_m(s - \Sigma_{q \neq m} s_q M_q(i)) + \lambda(1 - \Sigma_{q \neq m} M_q(i)) - \alpha w_m(i)}{w_m^g \Sigma_{D1} / \psi(D) + \beta(p_m^2 + s_m^2) + \lambda}$$

where D is the set of directions {E, N, W, S, U, D}, i is the index of the current voxel in the volume, and the weight of direction 'E' is given as follows:

$$\psi(E) = \sqrt{\frac{(M_m(E) - M_m(i))^2}{d_y^2} + \frac{(M_m(NE) - M_m(SE) + M_m(N) - M_m(S))^2}{(4d_x)^2} + \frac{(M_m(U) + M_m(EU) - M_m(D) - M_m(ED))^2}{(4d_z)^2} + \varepsilon,}$$

where $\varepsilon$ is a small number, e.g., $\varepsilon$=0.001, and $d_x$, $d_y$ & $d_z$ are the voxel dimensions.

The weights for the other directions are derived in an analogous manner.

if $M_m(i) < 0$ than set $M_m(i)=0$ end

Algorithm Outputs

The algorithm output is a volume fraction map, $M_i$, for each material i, i.e., the volume fraction of material i in the mix of materials of the scanned object. In addition, $p_i M_i$ and $s_i M_i$ are the attenuation coefficient contribution of material i to the Photoelectric and Compton scattering images, correspondingly.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for multi material decomposition of an object, comprising:

an input unit;

a processing unit; and an output unit;

wherein the input unit is configured to provide the processing unit with at least one image of an object, wherein the at least one image is derived from at least one dual energy spectral X-ray image of the object, and wherein the at least one image comprises a Photoelectric total attenuation coefficient image and a Compton scattering total attenuation coefficient image;

wherein the input unit is configured to provide the processing unit with a plurality of Photoelectric attenuation coefficients for a plurality of materials, each Photoelectric attenuation coefficient being associated with a corresponding material;

wherein the input unit is configured to provide the processing unit with a plurality of Compton scattering attenuation coefficients for the plurality of materials, each Compton scattering attenuation coefficient being associated with a corresponding material;

wherein the processing unit is configured to set a total volume constraint at an image location in the at least one image as a function of the sum of individual volumes of the plurality of materials at the image location;

wherein the processing unit is configured to determine volume fractions of the plurality of materials at the image location according to an overall function comprising: a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint;

wherein an iterative minimization algorithm is used to solve the overall function;

wherein the plurality of materials comprises at least four materials; and wherein the output unit is configured to output data representative of the volume fractions of the plurality of materials.

2. Apparatus according to claim 1, wherein the overall function comprises a Total Variation term determined according to a function comprising the plurality of Photoelectric attenuation coefficients for the plurality of materials and the plurality of Compton scattering attenuation coefficients for the plurality of materials.

3. Apparatus according to claim 2, wherein the Total Variation term comprises a Photoelectric coefficient for a material of the plurality of materials being added to a Compton scattering coefficient for that material.

4. Apparatus according to claim 3, wherein the Total Variation term comprises a summation over the plurality of materials, wherein the summation comprises each Photoelectric coefficient for the plurality of materials being added to a corresponding Compton scattering coefficient for the plurality of materials.

5. Apparatus according to claim 1, wherein the overall function comprises a Sparsity term determined according to a function comprising: the Photoelectric total attenuation coefficient at the image location; the Compton scattering total attenuation coefficient at the image location; the plurality of Photoelectric attenuation coefficients for the plurality of materials; and the plurality of Compton scattering attenuation coefficients for the plurality of materials.

6. Apparatus according to claim 5, wherein the Sparsity term comprises the Photoelectric total attenuation coefficient at the image location being subtracted from a Photoelectric attenuation coefficient for a material of the plurality of materials, and wherein the Sparsity term comprises the Compton scattering total attenuation coefficient at the image location being subtracted from a Compton scattering attenuation coefficient for the material of the plurality of materials.

7. Apparatus according to claim 5, wherein the Sparsity term comprises information about the expected volume fraction of at least one of the materials.

8. Apparatus according to claim 1, wherein the overall function comprises a data fidelity term determined according to a function comprising: the Photoelectric total attenuation coefficient at the image location; the Compton scattering total attenuation coefficient at the image location; the plurality of Photoelectric attenuation coefficients for the plurality of materials; and the plurality of Compton scattering attenuation coefficients for the plurality of materials.

9. Apparatus according to claim 8, wherein the data fidelity term comprises a summation over all of the materials of a Photoelectric attenuation coefficient for a material of the plurality of materials multiplied by a volume fraction of that material, wherein this summation is subtracted from the Photoelectric total attenuation coefficient at the image location; and wherein the data fidelity term comprises a summation over all of the materials of a Compton scattering attenuation coefficient for a material of the plurality of materials multiplied by a volume fraction of that material, wherein this summation is subtracted from the Compton scattering total attenuation coefficient at the image location.

10. Apparatus according to claim 1, wherein, the processing unit is configured to generate the at least one image of the object from a decomposition of the at least one spectral X-ray image of the object.

11. A medical system for multi material decomposition of an object, the system comprising:
    an image acquisition unit; and
    an apparatus for multi material decomposition of an object according to claim 1;
    wherein the image acquisition unit is configured to acquire the at least one dual energy spectral X-ray image of the object;
    wherein the processing unit is configured to determine volume fractions of the plurality of materials at a plurality of image locations; and
    wherein the output unit is configured to output at least one image of the object on the basis of the plurality of volume fractions of the plurality of materials.

12. A method for multi material decomposition of an object, comprising:
    providing at least one image of an object, wherein the at least one image is derived from at least one dual energy spectral X-ray image of the object, and wherein the at least one image comprises a Photoelectric total attenuation coefficient image and a Compton scattering total attenuation coefficient image;
    providing a plurality of Photoelectric attenuation coefficients for a plurality of materials, each Photoelectric attenuation coefficient being associated with a corresponding material;
    providing a plurality of Compton scattering attenuation coefficients for the plurality of materials, each Compton scattering attenuation coefficient being associated with a corresponding material;
    setting a total volume constraint at an image location in the at least one image as a function of the sum of individual volumes of the plurality of materials at the image location;
    determining volume fractions of the plurality of materials at the image location according to an overall function comprising: a Photoelectric total attenuation coefficient at the image location taken from the Photoelectric total attenuation coefficient image; a Compton scattering total attenuation coefficient at the image location taken from the Compton scattering total attenuation coefficient image; the plurality of Photoelectric attenuation coefficients for the plurality of materials; the plurality of Compton scattering attenuation coefficients for the plurality of materials; and the total volume constraint, wherein an iterative minimization algorithm is used to solve the overall function; and
    outputting data representative of the volume fractions of the plurality of materials, wherein the plurality of materials comprises at least four materials.

13. A non-transitory computer readable medium encoded with a computer program for controlling an apparatus, which when executed by a processor is configured to carry out the method of claim 12.

* * * * *